(12) United States Patent
Himmelsbach et al.

(10) Patent No.: US 7,223,749 B2
(45) Date of Patent: May 29, 2007

(54) BICYCLIC HETEROCYCLES, PHARMACEUTICAL COMPOSITIONS CONTAINING THESE COMPOUNDS, THEIR USE AND PROCESSES FOR PREPARING THEM

(75) Inventors: Frank Himmelsbach, Mittelbiberach (DE); Flavio Solca, Vienna (AT)

(73) Assignee: Boehringer Ingelheim International GmbH, Ingelheim (DE)

( * ) Notice: Subject to any disclaimer, the term of this patent is extended or adjusted under 35 U.S.C. 154(b) by 95 days.

(21) Appl. No.: 10/778,985

(22) Filed: Feb. 13, 2004

(65) Prior Publication Data

US 2005/0107358 A1    May 19, 2005

Related U.S. Application Data

(60) Provisional application No. 60/452,280, filed on Mar. 5, 2003.

(30) Foreign Application Priority Data

Feb. 20, 2003  (DE) ................ 103 07 165

(51) Int. Cl.
C07D 267/10 (2006.01)
A61K 31/553 (2006.01)

(52) U.S. Cl. ................. 514/211.15; 540/544

(58) Field of Classification Search ........... 540/544; 514/211.15
See application file for complete search history.

(56) References Cited

U.S. PATENT DOCUMENTS

| | | | |
|---|---|---|---|
| 5,866,572 A | 2/1999 | Barker et al. | |
| 6,127,374 A | 10/2000 | Bridges | |
| 6,153,617 A | 11/2000 | Bridges | |
| 6,251,912 B1 | 6/2001 | Wissner et al. | |
| 6,344,459 B1 | 2/2002 | Bridges et al. | |
| 6,384,035 B1 * | 5/2002 | Hutchings et al. | 514/252.13 |
| 6,627,634 B2 | 9/2003 | Himmelsbach et al. | |
| 6,653,305 B2 | 11/2003 | Himmelsbach et al. | |
| 6,673,803 B2 | 1/2004 | Thomas et al. | |
| 7,019,012 B2 | 3/2006 | Himmelsbach et al. | |
| 2001/0044435 A1 | 11/2001 | Himmelsbach et al. | |
| 2002/0032208 A1 | 3/2002 | Lohmann et al. | |
| 2002/0077330 A1 | 6/2002 | Himmelsbach et al. | |
| 2002/0169180 A1 | 11/2002 | Himmelsbach et al. | |
| 2002/0173509 A1 | 11/2002 | Himmelsbach et al. | |
| 2002/0177601 A1 | 11/2002 | Himmelsbach et al. | |
| 2003/0149062 A1 | 8/2003 | Jung et al. | |
| 2003/0191308 A1 | 10/2003 | Hennequin et al. | |
| 2004/0024019 A1 | 2/2004 | Tanimoto et al. | |

FOREIGN PATENT DOCUMENTS

| | | |
|---|---|---|
| DE | 19908567 | 2/1999 |
| DE | 19911366 | 3/1999 |
| DE | 10042060 A1 | 3/2002 |
| EP | 0566226 | 10/1993 |
| WO | WO9520045 | 7/1995 |
| WO | WO9630347 | 10/1996 |
| WO | WO9633980 | 10/1996 |
| WO | WO9702266 | 1/1997 |
| WO | WO9738983 | 10/1997 |
| WO | WO9843960 | 10/1998 |
| WO | WO9906378 | 2/1999 |
| WO | WO9906396 | 2/1999 |
| WO | WO9909016 | 2/1999 |
| WO | WO9935146 | 7/1999 |
| WO | WO0018740 | 4/2000 |
| WO | WO0031068 | 6/2000 |
| WO | WO0051991 | 9/2000 |
| WO | WO0055141 | 9/2000 |
| WO | WO0078735 | 12/2000 |
| WO | WO0177104 | 10/2001 |
| WO | WO 02/50043 A1 | 6/2002 |

OTHER PUBLICATIONS

Ulrich, L. et al; Human epidermal growth factor receptor cDNA sequence and aberrant expression of the amplidied gene in A431 epidermoid carcinoma cells, "NATURE" vol. 309, May 1984, 418-425.

(Continued)

Primary Examiner—Joseph K. McKane
Assistant Examiner—Nyeemah Grazier
(74) Attorney, Agent, or Firm—Michael P. Morris; Mary-Ellen M. Devlin; Timothy X Witkowski

(57) ABSTRACT

The present invention relates to bicyclic heterocycles of general formula

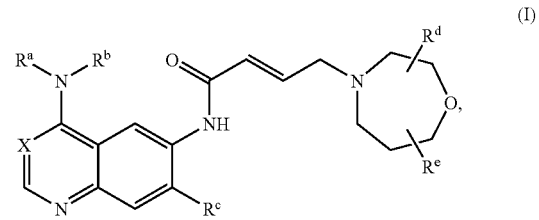

(I)

wherein
$R^a$, $R^b$, $R^c$, $R^d$, $R^e$ and X are defined as in claim 1, the tautomers, the stereoisomers, the mixtures thereof and the salts thereof, particularly the physiologically acceptable salts thereof with inorganic or organic acids, which have valuable pharmacological properties, particularly an inhibitory effect on signal transduction mediated by tyrosine kinases, the use thereof for treating diseases, particularly tumoral diseases and benign prostatic hyperplasia (BPH), diseases of the lungs and respiratory tract, and the preparation thereof.

7 Claims, No Drawings

OTHER PUBLICATIONS

International Search Report Reference No. PCT/EP 2004/001398.
Tsou, H. et al: 6-Substituted-4-(3-bromophenylamino)quinazolines as Putative Irreversible Inhibitors of the epidermal Growth Factor Receptor (EGFR) and Human Epidermal Growth Factor Receptor (HER-2) Tyrosine Kinases with Enhanced Antitumor Activity; J. Med. Chem. 2001; vol. 44, pp. 2719-2734.

* cited by examiner

BICYCLIC HETEROCYCLES, PHARMACEUTICAL COMPOSITIONS CONTAINING THESE COMPOUNDS, THEIR USE AND PROCESSES FOR PREPARING THEM

The present invention relates to bicyclic heterocycles of general formula

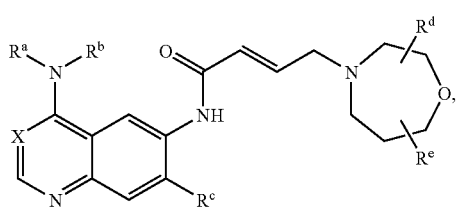

the tautomers, the stereoisomers, the mixtures thereof and the salts thereof, particularly the physiologically acceptable salts thereof with inorganic or organic acids, which have valuable pharmacological properties, particularly an inhibitory effect on signal transduction mediated by tyrosine kinases, the use thereof for treating diseases, particularly tumoral diseases and benign prostatic hyperplasia (BPH), diseases of the lungs and respiratory tract, and the preparation thereof.

In the above general formula I $R^a$ denotes a hydrogen atom or a $C_{1-4}$-alkyl group, $R^b$ denotes a phenyl, benzyl or 1-phenylethyl group, wherein the phenyl nucleus in each case is substituted by the groups $R^1$ to $R^3$, while $R^1$ and $R^2$, which may be identical or different, in each case denote a hydrogen, fluorine, chlorine, bromine or iodine atom, a $C_{1-4}$-alkyl, hydroxy, $C_{1-4}$-alkoxy, $C_{2-3}$-alkenyl or $C_{2-3}$-alkynyl group, an aryl, aryloxy, arylmethyl or arylmethoxy group, a heteroaryl, heteroaryloxy, heteroarylmethyl or heteroarylmethoxy group, a methyl or methoxy group substituted by 1 to 3 fluorine atoms or a cyano, nitro or amino group, and $R^3$ denotes a hydrogen, fluorine, chlorine or bromine atom, a methyl or trifluoromethyl group, $R^c$ denotes a hydrogen atom or a fluorine, chlorine or bromine atom, a hydroxy or $C_{1-4}$-alkyloxy group, a methoxy group substituted by 1 to 3 fluorine atoms, an ethyloxy group substituted by 1 to 5 fluorine atoms, a $C_{2-4}$-alkyloxy group which is substituted by a group $R^4$, while $R^4$ denotes a hydroxy, $C_{1-3}$-alkyloxy, $C_{3-6}$-cycloalkyloxy, $C_{3-6}$-cycloalkyl-$C_{1-3}$-alkyloxy, amino, $C_{1-3}$-alkylamino, di-($C_{1-3}$-alkyl)amino, bis-(2-$C_{1-3}$-alkyloxy-ethyl)-amino, bis-(3-$C_{1-3}$-alkyloxy-propyl)-amino, pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl or 4-($C_{1-3}$-alkyl)-homopiperazin-1-yl group, a $C_{3-7}$-cycloalkyloxy or $C_{3-7}$-cycloalkyl-$C_{1-4}$-alkyloxy group, a tetrahydrofuran-3-yloxy, tetrahydropyran-3-yloxy or tetrahydropyran-4-yloxy group, a tetrahydrofuranyl-$C_{1-4}$-alkyloxy or tetrahydropyranyl-$C_{1-4}$-alkyloxy group, a pyrrolidin-3-yloxy, piperidin-3-yloxy or piperidin-4-yloxy group, a 1-($C_{1-3}$-alkyl)-pyrrolidin-3-yloxy, 1-($C_{1-3}$-alkyl)-piperidin-3-yloxy or 1-($C_{1-3}$-alkyl)-piperidin-4-yloxy group, a $C_{1-4}$-alkoxy group which is substituted by a pyrrolidinyl, piperidinyl or homopiperidinyl group substituted in the 1 position by the group $R^5$, where $R^5$ denotes a hydrogen atom or a $C_{1-3}$-alkyl group, or a $C_{1-4}$-alkoxy group which is substituted by a morpholinyl or homomorpholinyl group substituted in the 4 position by the group $R^5$, where $R^5$ is as hereinbefore defined, $R^e$ and $R^d$, which may be identical or different, in each case denote a hydrogen atom or a $C_{1-3}$-alkyl group and X denotes a methyne group substituted by a cyano group or a nitrogen atom, while by the aryl groups mentioned in the definition of the above groups is meant in each case a phenyl group which is mono- or disubstituted by $R^6$, while the substituents may be identical or different and $R^6$ denotes a hydrogen atom, a fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group, by the heteroaryl groups mentioned in the definition of the above groups is meant a pyridinyl, pyridazinyl, pyrimidinyl or pyrazinyl group, while the above-mentioned heteroaryl groups are mono- or disubstituted in each case by the group $R^6$, while the substituents may be identical or different and $R^6$ is as hereinbefore defined, and unless otherwise stated, the above-mentioned alkyl groups may be straight-chain or branched.

Preferred compounds of the above general formula I are those wherein $R^a$ denotes a hydrogen atom, $R^b$ denotes a phenyl group substituted by the groups $R^1$ to $R^3$, while $R^1$ denotes a hydrogen, fluorine, chlorine or bromine atom, a methyl, trifluoromethyl or ethynyl group, a phenyloxy or phenylmethoxy group, while the phenyl moiety of the above-mentioned groups is optionally substituted by a fluorine or chlorine atom, or a pyridinyloxy or pyridinylmethoxy group, while the pyridinyl moiety of the above-mentioned groups is optionally substituted by a methyl or trifluoromethyl group, $R^2$ denotes a hydrogen, fluorine or chlorine atom and $R^3$ denotes a hydrogen atom, $R^c$ denotes a hydrogen atom, a $C_{1-3}$-alkyloxy group, a $C_{4-6}$-cycloalkyloxy or $C_{3-6}$-cycloalkyl-$C_{1-2}$-alkyloxy group, a tetrahydrofuran-3-yloxy, tetrahydropyran-3-yloxy, tetrahydropyran-4-yloxy, tetrahydrofuranyl-$C_{1-2}$-alkyloxy or tetrahydropyranyl-$C_{1-2}$-alkyloxy group, an ethyloxy group which is substituted in the 2 position by a group $R^4$, where $R^4$ denotes a hydroxy, $C_{1-3}$-alkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, piperazin- 1-yl, 4-(C$_{1-3}$-alkyl)-piperazin-1-yl, homopiperazin-1-yl or 4-(C$_{1-3}$-alkyl)-homopiperazin-1-yl group, a propyloxy group which is substituted by a group R$^4$ in the 3 position, while R$^4$ is as hereinbefore defined, or a butyloxy group which is substituted by a group R$^4$ in the 4 position, while R$^4$ is as hereinbefore defined, R$^e$ and R$^d$, which may be identical or different, in each case denote a hydrogen atom or a methyl group and X denotes a nitrogen atom, while, unless otherwise stated, the above-mentioned alkyl groups may be straight-chain or branched, the tautomers, their stereoisomers, the mixtures thereof and the salts thereof.

Particularly preferred compounds of the above general formula I are those wherein R$^a$ denotes a hydrogen atom, R$^b$ denotes a 3-ethynylphenyl, 3-bromophenyl, 3,4-difluorophenyl or 3-chloro-4-fluoro-phenyl group, R$^c$ denotes a hydrogen atom, a methoxy, ethyloxy, 2-(methoxy)ethyloxy, 3-(morpholin-4-yl)propyloxy, cyclobutyloxy, cyclopentyloxy, cyclohexyloxy, cyclopropylmethoxy, cyclopentylmethoxy, tetrahydrofuran-3-yloxy, tetrahydropyran-3-yloxy, tetrahydropyran-4-yloxy, tetrahydrofuran-2-ylmethoxy, tetrahydrofuran-3-ylmethoxy or tetrahydropyran-4-ylmethoxy group, R$^e$ and R$^d$ in each case denote a hydrogen atom and X denotes a nitrogen atom, the tautomers, their stereoisomers, the mixtures thereof and the salts thereof.

Most particularly preferred compounds of general formula I are those wherein

R$^a$ denotes a hydrogen atom,

R$^b$ denotes a 3-chloro-4-fluoro-phenyl group,

R$^c$ denotes a tetrahydrofuran-3-yloxy group,

R$^e$ and R$^d$ in each case denote a hydrogen atom and

X denotes a nitrogen atom, the tautomers, their stereoisomers, the mixtures thereof and the salts thereof.

The following particularly preferred compound of general formula I is mentioned by way of example:

4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline and the salts thereof.

The compounds of general formula I may be prepared by the following methods, for example:

a) reacting a compound of general formula

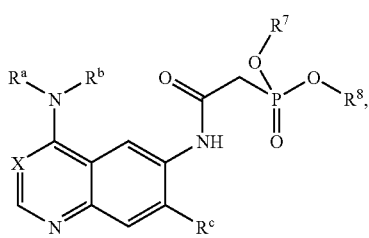

(II)

wherein

R$^a$, R$^b$, R$^c$ and X are as hereinbefore defined and R$^7$ and R$^8$, which may be identical or different, denote C$_{1-4}$-alkyl groups, with a compound of general formula

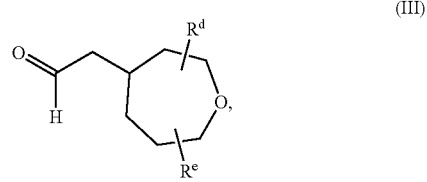

(III)

wherein

R$^d$ and R$^e$ are as hereinbefore defined.

The reaction is expediently carried out in a solvent or mixture of solvents such as tetrahydrofuran, tetrahydrofuran/water, acetonitrile, acetonitrile/water, dioxane, ethyleneglycol dimethyl ether, isopropanol, methylene chloride, dimethylformamide or sulpholane, optionally in the presence of an inorganic or organic base, e.g. sodium carbonate, potassium hydroxide or 1,8-diazabicyclo[5.4.0]undec-7-ene and optionally in the presence of a lithium salt such as lithium chloride at temperatures between –50 and 150° C., but preferably at temperatures between –20 and 80° C. The reaction may also be carried out with a reactive derivative of the compound of general formula III, for example the hydrate or a hemiacetal.

b) reacting a compound of general formula

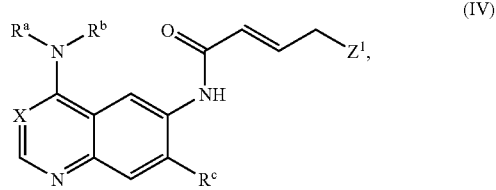

(IV)

wherein

R$^a$, R$^b$, R$^c$ and X are as hereinbefore defined and Z$^1$ denotes a leaving group such as a halogen atom or a substituted sulphonyloxy group such as a chlorine or bromine atom, a methanesulphonyloxy or p-toluenesulphonyloxy group, with a compound of general formula

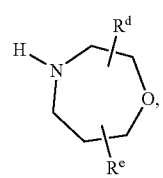

(V)

wherein R$^d$ and R$^e$ are as hereinbefore defined.

The reaction is expediently carried out in a solvent such as isopropanol, butanol, tetrahydrofuran, dioxane, acetonitrile, dimethylformamide, sulpholane, toluene or methylene chloride or mixtures thereof, optionally in the presence of an inorganic or organic base, e.g. sodium carbonate, potassium carbonate, potassium hydroxide, triethylamine or N-ethyl-diisopropylamine and optionally in the presence of a reaction accelerator such as an alkali metal iodide at temperatures between −20 and 150° C., but preferably at temperatures between 0 and 100° C. The reaction may however also be carried out without a solvent or in an excess of the compound of general formula V used.

In the reactions described hereinbefore, any reactive groups present such as hydroxy, amino, alkylamino or imino groups may be protected during the reaction by conventional protecting groups which are cleaved again after the reaction.

For example, a protecting group for a hydroxy group may be a trimethylsilyl, acetyl, trityl, benzyl or tetrahydropyranyl group.

Protecting groups for an amino, alkylamino or imino group may be a formyl, acetyl, trifluoroacetyl, ethoxycarbonyl, tert. butoxycarbonyl, benzyloxycarbonyl, benzyl, methoxybenzyl or 2,4-dimethoxybenzyl group.

Any protecting group used is optionally subsequently cleaved for example by hydrolysis in an aqueous solvent, e.g. in water, isopropanol/water, acetic acid/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or aprotically, e.g. in the presence of iodotrimethylsilane, at temperatures between 0 and 120° C., preferably at temperatures between 10 and 100° C.

However, a benzyl, methoxybenzyl or benzyloxycarbonyl group is cleaved, for example, hydrogenolytically, e.g. with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0 and 100° C., but preferably at temperatures between 20 and 60° C., and at a hydrogen pressure of 1 to 7 bar, but preferably 3 to 5 bar. A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid or by treating with iodotrimethylsilane, optionally using a solvent such as methylene chloride, dioxane, methanol or diethylether.

A trifluoroacetyl group is preferably cleaved by treating with an acid such as hydrochloric acid, optionally in the presence of a solvent such as acetic acid at temperatures between 50 and 120° C. or by treating with sodium hydroxide solution optionally in the presence of a solvent such as tetrahydrofuran at temperatures between 0 and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-O-p-tolyltartaric acid, malic acid, mandelic acid, camphorsulphonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, methanesulphonic acid, phosphoric acid, fumaric acid, succinic acid, lactic acid, citric acid, tartaric acid or maleic acid.

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerisation or tyrosinekinase itself. It is also possible to block the transmission of signals to components located further downstream.

The biological properties of the new compounds were investigated as follows:

The inhibition of human EGF-receptor kinase was determined using the cytoplasmatic tyrosine kinase domain (methionine 664 to alanine 1186, based on the sequence published in Nature 309 (1984), 418). To do this, the protein was expressed in Sf9 insect cells as a GST fusion protein using the Baculovirus expression system.

The enzyme activity was measured in the presence or absence of the test compounds in serial dilutions. The polymer pEY (4:1) produced by SIGMA was used as the substrate. Biotinylated pEY (bio-pEY) was added as the tracer substrate. Every 100 µl of reaction solution contained 10 µl of the inhibitor in 50% DMSO, 20 µl of the substrate solution (200 mM HEPES pH 7.4, 50 mM magnesium acetate, 2.5 mg/ml of poly(EY), 5 µg/ml of bio-pEY) and 20 µl of enzyme preparation. The enzyme reaction was started by the addition of 50 µl of a 100 µM ATP solution in 10 mM magnesium chloride. The dilution of the enzyme preparation was adjusted so that the incorporation of phosphate into the bio-pEY was linear in terms of time and quantity of enzyme. The enzyme preparation was diluted in 20 mM HEPES pH 7.4, 1 mM EDTA, 130 mM common salt, 0.05% Triton X-100, 1 mM DTT and 10% glycerol.

The enzyme assays were carried out at ambient temperature over a period of 30 minutes and were ended by the addition of 50 µl of a stopping solution (250 mM EDTA in 20 mM HEPES pH 7.4). 100 µl were placed on a streptavidin-coated microtitre plate and incubated for 60 minutes at ambient temperature. Then the plate was washed with 200 µl of a washing solution (50 mM Tris, 0.05% Tween 20). After the addition of 100 µl of a HRPO-labelled anti-PY antibody (PY20H Anti-PTyr:HRP produced by Transduction Laboratories, 250 ng/ml) it was incubated for 60 minutes. Then the microtitre plate was washed three times with 200 µl of washing solution. The samples were then combined with 100 µl of a TMB-peroxidase solution (A:B=1:1, Kirkegaard Perry Laboratories). After 10 minutes the reaction was stopped. The extinction was measured at $OD_{450\ nm}$ with an ELISA reader. All data points were measured three times.

The data were matched using an iterative calculation using an analytical programme for sigmoidal curves (Graph Pad Prism Version 3.0; sigmoid curves, variable pitch). All the iteration data released showed a correlation coefficient of more than 0.9. The maxima and minima of the curves showed a spread of at least a factor of 5. The $IC_{50}$ (concentration of active substance which inhibits the activity of EGF-receptor kinase by 50%) was determined from the curves.

The following results were obtained:

| Compound (Example No.) | Inhibition of EGF-receptor kinase $IC_{50}$ [nM] |
| --- | --- |
| 1 | 1.5 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g. benign or malignant tumours, particularly tumours of epithelial and neuroepithelial origin, metastasisation and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g. in inflammatory diseases of the airways such as chronic bronchitis, chronic obstructive bronchitis, asthma, bronchiectasis, allergic or non-allergic rhinitis or sinusitis, cystic fibrosis, α1-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g. in chronic inflammatory changes such as cholecystitis, Crohn's disease, ulcerative colitis, and ulcers in the gastrointestinal tract or such as may occur in diseases of the gastrointestinal tract which are associated with increased secretions, such as Men6trier's disease, secreting adenomas and protein loss syndrome.

In addition, the compounds of general formula I and the physiologically acceptable salts thereof may be used to treat other diseases caused by abnormal function of tyrosine kinases, such as e.g. epidermal hyperproliferation (psoriasis), benign prostatic hyperplasia (BPH), inflammatory processes, diseases of the immune system, hyperproliferation of haematopoietic cells, treatment of nasal polyps, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g. etoposide), mitosis inhibitors (e.g. vinblastine), compounds which interact with nucleic acids (e.g. cis-platin, cyclophosphamide, adriamycin), hormone antagonists (e.g. tamoxifen), inhibitors of metabolic processes (e.g. 5-FU etc.), cytokines (e.g. interferons), antibodies, etc. For treating respiratory tract diseases, these compounds may be used on their own or in conjunction with other therapeutic agents for the airways, such as substances with a secretolytic (e.g. ambroxol, N-acetylcysteine), broncholytic (e.g. tiotropium or ipratropium or fenoterol, salmeterol, salbutamol) and/or anti-inflammatory activity (e.g. theophylline or glucocorticoids). For treating diseases in the region of the gastrointestinal tract, these compounds may also be administered on their own or in conjunction with substances having an effect on motility or secretion. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:

Preparation of the Starting Compounds:

EXAMPLE I

4-[(3-chloro-4-fluoro-phenyl)amino]-6-[(diethoxy-phosphoryl)-acetylamino]-7-[(S)-(tetrahydrofuran-3-yl)oxy]-quinazoline 60.07 g of diethoxyphosphorylacetic acid are placed in 750 ml of N,N-dimethylformamide and at ambient temperature combined with 48.67 g of N,N'-carbonyldiimidazole. After the development of gas has ceased 90.00 g of 4-[(3-chloro-4-fluoro-phenyl)amino]-6-amino-[(S)-(tetrahydrofuran-3-yl)oxy]-quinazoline are added and the reaction mixture is stirred for about 4–5 hours at ambient temperature until the reaction is complete. The reaction mixture is then heated gently in the water bath and 750 ml of water are added twice. The thick suspension is stirred overnight and the next morning another 350 ml of water are added. The suspension is cooled in the ice bath, stirred for one hour and suction filtered. The filter cake is washed again with 240 ml of N,N-dimethylformamide/water (1:2) and 240 ml of diisopropylether and dried at 40° C. in the circulating air dryer.

The following compounds are obtained analogously to Example I:

(1) 4-[(3-chloro-4-fluoro-phenyl)amino]-6-[(diethoxy-phosphoryl)-acetylamino]-7-[(R)-(tetrahydrofuran-3-yl)oxy]-quinazoline Mass spectrum (ESI+): m/z=553, 555 [M+H]$^+$ (2) 4-[(3-chloro-4-fluoro-phenyl)amino]-6-[(diethoxy-phosphoryl)-acetylamino]-7-cyclopropylmethoxy-quinazoline melting point: 185–187° C.

(3) 4-[(3-bromophenyl)amino]-6-[(diethoxy-phosphoryl)-acetylamino]-quinazoline

Mass spectrum (ESI$^-$): m/z=491, 493 [M–H]$^-$ (4) 4-[(3-chloro-4-fluoro-phenyl)amino]-6-[(diethoxy-phosphoryl)-acetylamino]-7-cyclopentyloxy-quinazoline $R_f$ value: 0.54 (silica gel, methylene chloride/ethanol=20:1)

EXAMPLE II

Homomorpholin-4-yl-acetaldehyde-hydrochloride

Prepared by stirring (2.5 hours) 4-(2,2-dimethoxy-ethyl)-homomorpholine with semiconcentrated hydrochloric acid at 80° C. The solution obtained is further reacted directly as in Example 1.

EXAMPLE III 4-(2,2-dimethoxy-ethyl)-homomorpholine

Prepared by stirring (5 hours) homomorpholine-hydrochloride with bromoacetaldehyde-dimethylacetal in the presence of potassium carbonate in N-methylpyrrolidinone at 80° C.

$R_f$ value: 0.2 (silica gel, ethyl acetate/methanol/conc. aqueous ammonia=90:10:1)

Preparation of the Final Compounds:

EXAMPLE 1

4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline

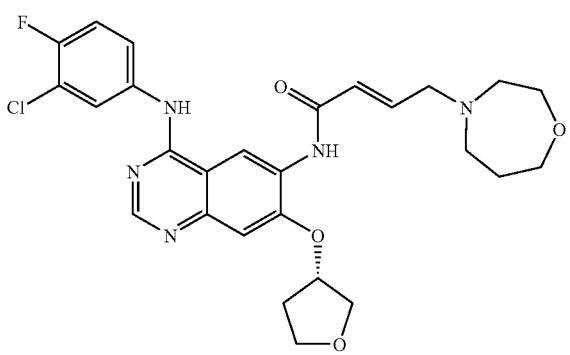

A solution of 3.9 g of 4-[(3-chloro-4-fluoro-phenyl)amino]-6-[2-(diethoxy-phosphoryl)-acetylamino]-7-[(S)-(tetrahydrofuran-3-yl)oxy]-quinazoline in 20 ml of tetrahydrofuran is added to a solution of 300 mg of lithium chloride in 20 ml of water at ambient temperature. Then 2.35 g of potassium hydroxide flakes are added and the reaction mixture is cooled to −3° C. in an ice/acetone cooling bath. The solution of the homomorpholin-4-yl-acetaldehyde hydrochloride obtained in Example II is then added dropwise within 5 min at a temperature of 0° C. After the addition has ended the reaction mixture is stirred for another 10 min at 0° C. and for a further hour at ambient temperature. For working up 100 ml of ethyl acetate are added and the aqueous phase is separated off. The organic phase is washed with saturated sodium chloride solution, dried over magnesium sulphate and evaporated down. The crude product is purified by chromatography over a silica gel column using ethyl acetate/methanol/conc. methanolic ammonia as eluant. The product obtained is stirred with a little diisopropyl ether, suction filtered and dried.

Yield: 2.40 g of (63% of theory)

$R_f$ value: 0.09 (silica gel, ethyl acetate/methanol/conc. aqueous ammonia=90:10:1)

Mass spectrum (ESI$^+$): m/z=542, 544 [M+H]$^+$

The following compounds may also be prepared analogously to the foregoing Examples and other methods known from the literature:

| Example No. | Structure |
|---|---|
| (1) | 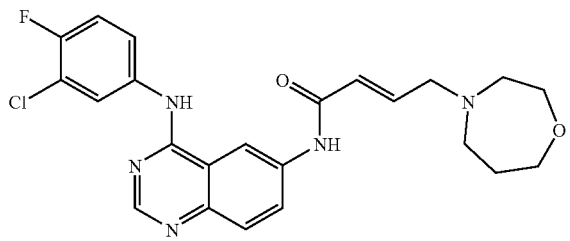 |

| Example No. | Structure |
|---|---|
| (2) | 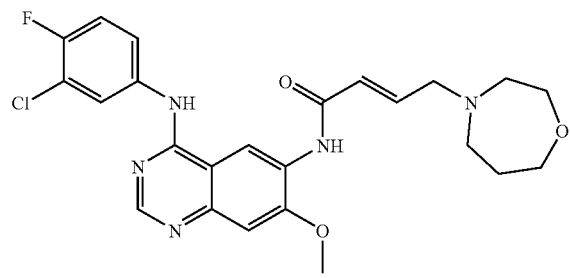 |
| (3) | 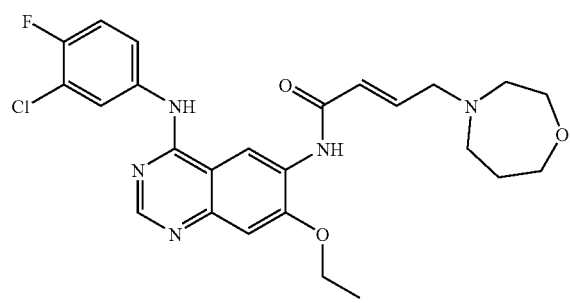 |
| (4) | 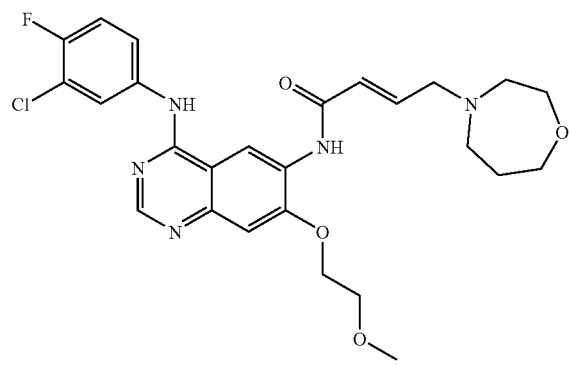 |
| (5) | 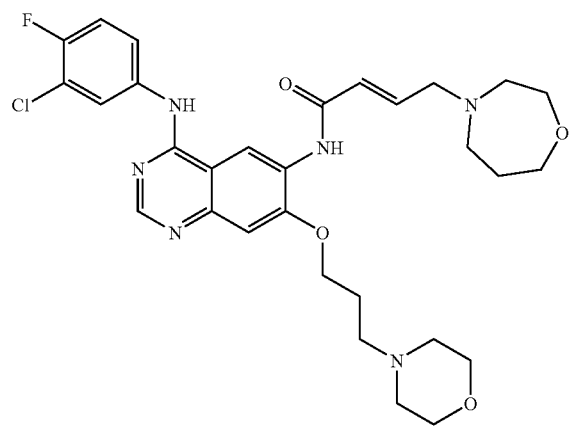 |

-continued
| Example No. | Structure |
|---|---|
| (6) | 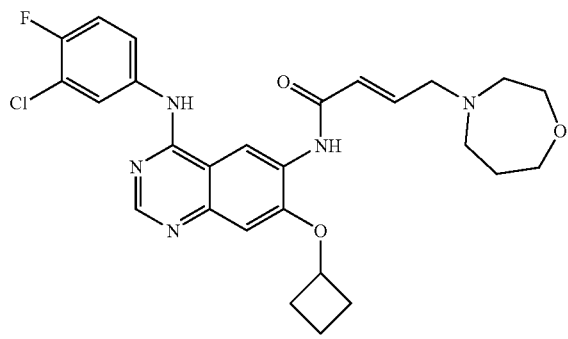 |
| (7) | 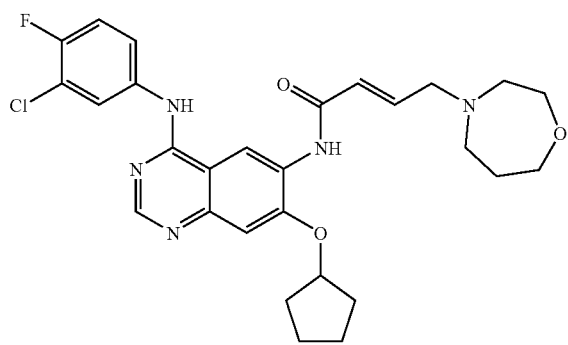 |
| (8) | 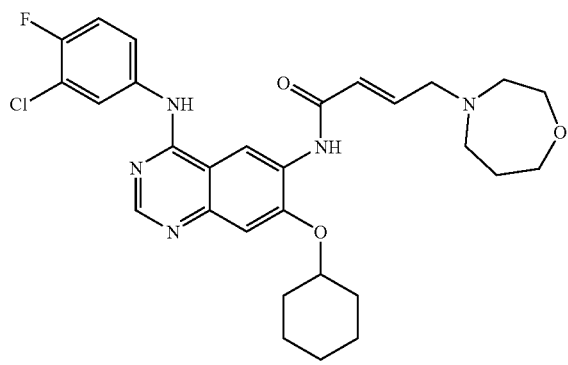 |
| (9) | 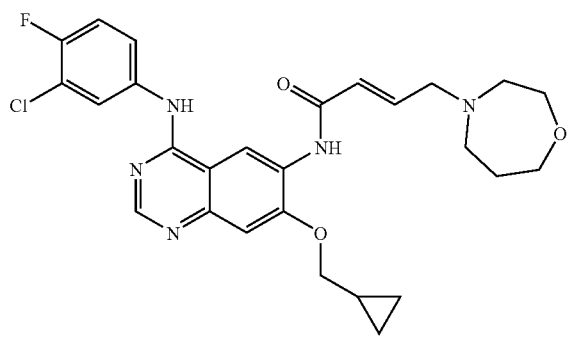 |

-continued
| Example No. | Structure |
|---|---|
| (10) | 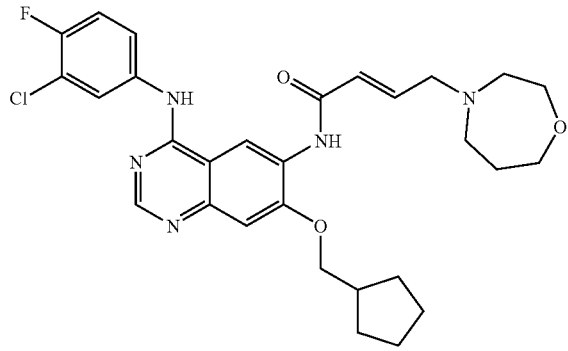 |
| (11) | 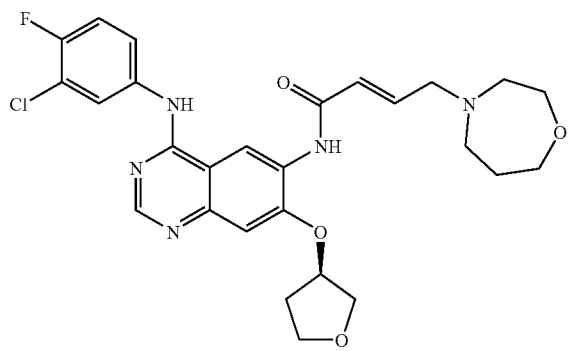 |
| (12) | 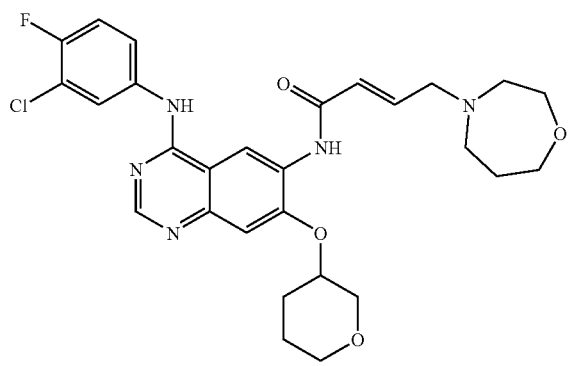 |
| (13) | 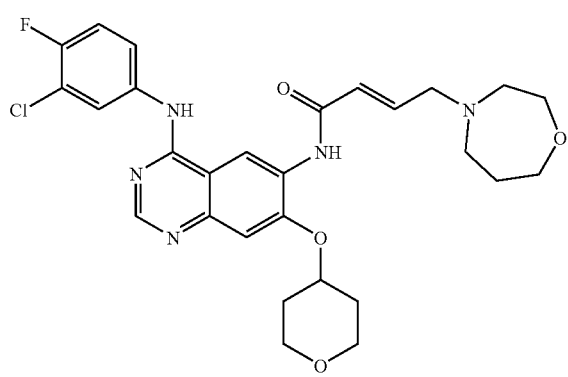 |

-continued
| Example No. | Structure |
|---|---|
| (14) | 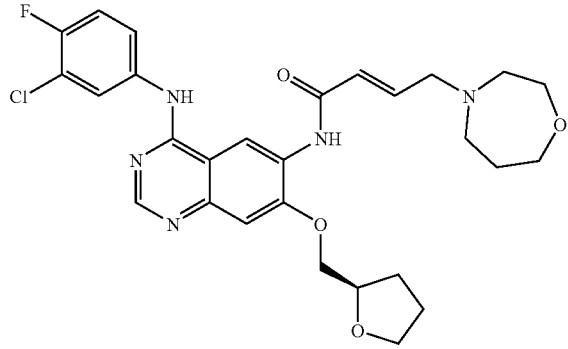 |
| (15) | 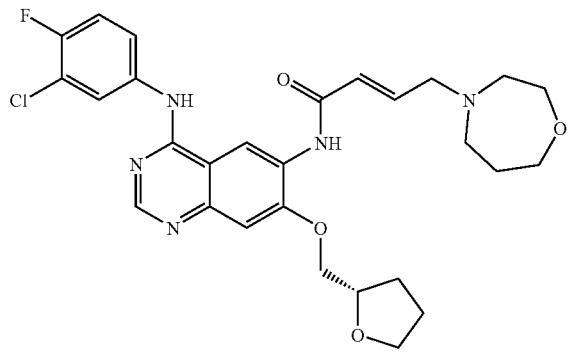 |
| (16) | 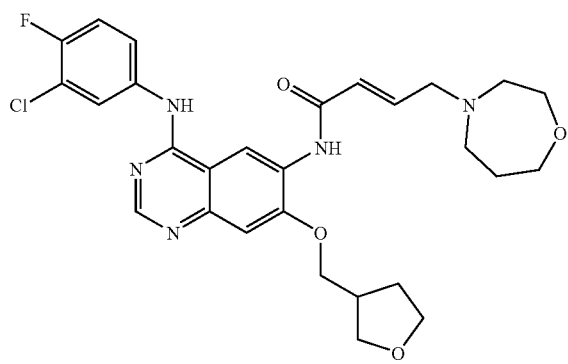 |
| (17) | 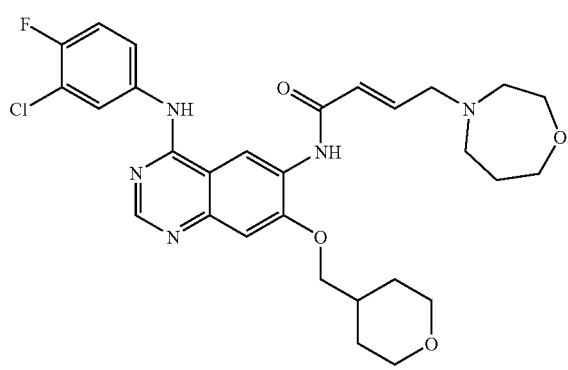 |

-continued
| Example No. | Structure |
|---|---|
| (18) | 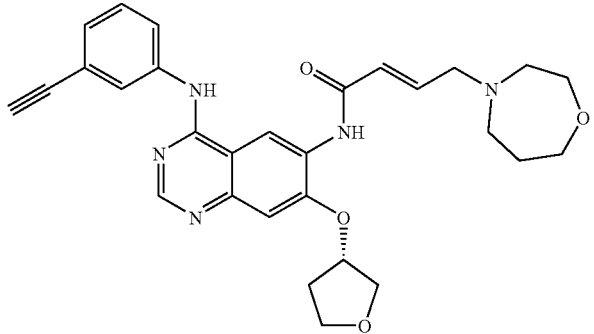 |
| (19) | 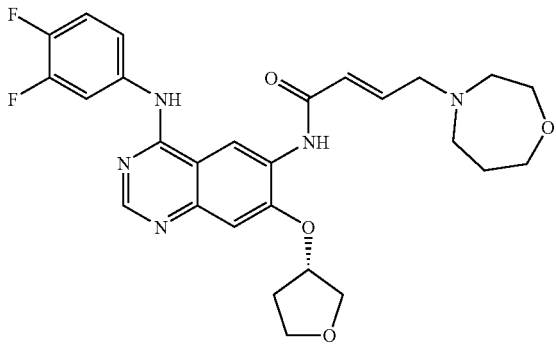 |
| (20) | 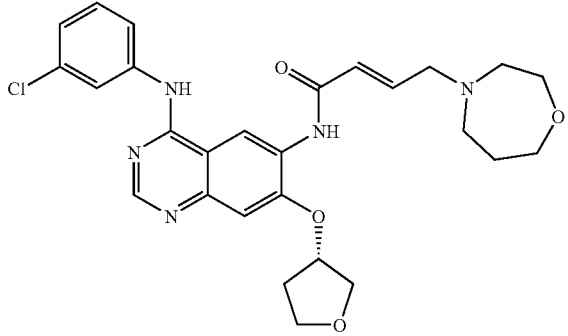 |
| (21) | 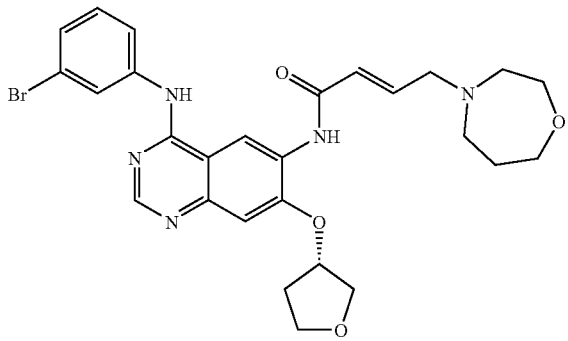 |

EXAMPLE 2

Coated Tablets Containing 75 mg of Active Substance

| 1 tablet core contains: | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

Weight of core: 230 mg die: 9 mm, convex

The tablet cores thus produced are coated with a film consisting essentially of hydroxypropylmethylcellulose. The finished film-coated tablets are polished with beeswax.

Weight of coated tablet: 245 mg.

EXAMPLE 3

Tablets Containing 100 mg of Active Substance

Composition:

| 1 tablet contains: | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

Weight of tablet: 220 mg

Diameter: 10 mm, biplanar, facetted on both sides and notched on one side.

EXAMPLE 4

Tablets Containing 150 mg of Active Substance

Composition:

| 1 tablet contains: | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

Weight of tablet: 300 mg die: 10 mm, flat

EXAMPLE 5

Hard Gelatine Capsules Containing 150 mg of Active Substance

| 1 capsule contains: | | |
|---|---|---|
| active substance | | 150.0 mg |
| corn starch (dried) | approx. | 180.0 mg |
| lactose (powdered) | approx. | 87.0 mg |
| magnesium stearate | | 3.0 mg |
| | approx. | 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules.

Capsule filling: approx. 320 mg

Capsule shell: size 1 hard gelatine capsule.

EXAMPLE 6

Suppositories Containing 150 mg of Active Substance

| 1 suppository contains: | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

23

Preparation:

After the suppository mass has been melted the active substance is homogeneously distributed therein and the melt is poured into chilled moulds.

EXAMPLE 7

Suspension Containing 50 mg of Active Substance

| 100 ml of suspension contain: | | |
| --- | --- | --- |
| active substance | | 1.00 g |
| carboxymethylcellulose-Na-salt | | 0.10 g |
| methyl p-hydroxybenzoate | | 0.05 g |
| propyl p-hydroxybenzoate | | 0.01 g |
| glucose | | 10.00 g |
| glycerol | | 5.00 g |
| 70% sorbitol solution | | 20.00 g |
| flavouring | | 0.30 g |
| dist. water | ad | 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavouring have been added and dissolved, the suspension is evacuated with stirring to eliminate air.

5 ml of suspension contain 50 mg of active substance.

EXAMPLE 8

Ampoules Containing 10 mg Active Substance

| Composition: | | |
| --- | --- | --- |
| active substance | | 10.0 mg |
| 0.01 N hydrochloric acid q.s. | | |
| double-distilled water | ad | 2.0 ml |

Preparation:

The active substance is dissolved in the requisite amount of 0.01 N HCl, made isotonic with common salt, filtered sterile and transferred into 2 ml ampoules.

EXAMPLE 9

Ampoules Containing 50 mg of Active Substance

| Composition: | | |
| --- | --- | --- |
| active substance | | 50.0 mg |
| 0.01 N hydrochloric acid q.s. | | |
| double-distilled water | ad | 10.0 ml |

Preparation:

The active substance is dissolved in the necessary amount of 0.01 N HCl, made isotonic with common salt, filtered sterile and transferred into 10 ml ampoules.

24

EXAMPLE 10

Capsules for Powder Inhalation Containing 5 mg of Active Substance

| 1 capsule contains: | |
| --- | --- |
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg). weight of capsule: 70.0 mg
size of capsule 3

EXAMPLE 11

Solution for Inhalation for Hand-held Nebulisers Containing 2.5 mg Active Substance

| 1 spray contains: | |
| --- | --- |
| active substance | 2.500 mg |
| benzalkonium chloride | 0.001 mg |
| 1N hydrochloric acid q.s. | |
| ethanol/water (50/50) | ad 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulisers (cartridges).

Contents of the container: 4.5 g

What is claimed is:

1. A bicyclic heterocycle of formula

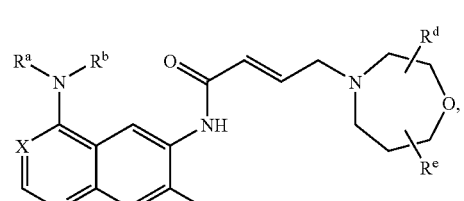

wherein
$R^a$ denotes a hydrogen atom or a $C_{1-4}$-alkyl group,
$R^b$ denotes a phenyl, benzyl or 1-phenylethyl group, wherein the phenyl nucleus in each case is substituted by the groups $R^1$ to $R^3$, wherein
$R^1$ and $R^2$ may be identical or different and denote a hydrogen, fluorine, chlorine, bromine or iodine atom,
a $C_{1-4}$-alkyl, hydroxy, $C_{1-4}$-alkoxy, $C_{2-3}$-alkenyl or $C_{2-3}$-alkynyl group,
an aryl, aryloxy, arylmethyl or arylmethoxy group, a heteroaryl, heteroaryloxy, heteroarylmethyl or heteroarylmethoxy group,
a methyl or methoxy group substituted by 1 to 3 fluorine atoms or
a pyrrolidin-3-yloxy, piperidin-3-yloxy or piperidin-4-yloxy group,
a 1-($C_{1-3}$-alkyl)-pyrrolidin-3-yloxy, 1-($C_{1-3}$-alkyl)-piperidin-3-yloxy or 1-($C_{1-3}$-alkyl)-piperidin-4-yloxy group,
a $C_{1-4}$-alkoxy group which is substituted by a pyrrolidinyl, piperidinyl or homopiperidinyl group substituted in the 1 position by the group $R^5$, wherein
$R^5$ denotes a hydrogen atom or a $C_{1-3}$-alkyl group,
or a $C_{1-4}$-alkoxy group which is substituted by a morpholinyl or homomorpholinyl group substituted in the 4 position by the group $R^5$, wherein $R^5$ is as hereinbefore defined,
$R^e$ and $R^d$ may be identical or different, and denote a hydrogen atom or a $C_{1-3}$-alkyl group
and
X denotes a methyne group substituted by a cyano group or a nitrogen atom,
wherein the aryl groups of the above R groups is a phenyl group which is mono- or disubstituted by the group $R^6$, wherein
$R^6$ may be identical or different and denote a hydrogen, fluorine, chlorine, bromine or iodine atom or a $C_{1-3}$-alkyl, hydroxy, $C_{1-3}$-alkyloxy, difluoromethyl, trifluoromethyl, difluoromethoxy, trifluoromethoxy or cyano group,
wherein the heteroaryl groups of the above R groups is a pyridinyl, pyridazinyl, pyrimidinyl or pyrazinyl group, which is mono- or disubstituted by the group $R^6$ wherein $R^6$ is as hereinbefore defined, and
a tautomer, stereoisomer, a mixture thereof or a salt thereof.

2. The bicyclic heterocycle of formula I according to claim 1, wherein
$R^a$ denotes a hydrogen atom,
$R^b$ denotes a phenyl group substituted by the groups $R^1$ to $R^3$, wherein
$R^1$ denotes a hydrogen, fluorine, chlorine or bromine atom,
a methyl, trifluoromethyl or ethynyl group,
a phenyloxy or phenylmethoxy group, wherein the phenyl moiety is optionally substituted by a fluorine or chlorine atom, or
a pyridinyloxy or pyridinylmethoxy group, wherein the pyridinyl moiety is optionally substituted by a methyl or trifluoromethyl group,
denotes a hydrogen, fluorine or chlorine atom and
$R^3$ denotes a hydrogen atom,
$R^c$ denotes a hydrogen atom,
a $C_{1-3}$-alkyloxy group,
a $C_{4-6}$-cycloalkyloxy or $C_{3-6}$-cycloalkyl-$C_{1-2}$-alkyloxy group,
a tetrahydrofuran-3-yloxy, tetrahydropyran-3-yloxy, tetrahydropyran-4-yloxy, tetrahydrofuranyl-$C_{1-2}$-alkyloxy or tetrahydropyranyl-$C_{1-2}$-alkyloxy group,
an ethyloxy group which is substituted in the 2 position by a group $R^4$, where $R^4$ denotes a hydroxy, $C_{1-3}$-alkyloxy, amino, $C_{1-3}$-alkylamino, di-($C_{1-3}$-alkyl)amino, bis-(2-methoxyethyl)-amino, pyrrolidin-1-yl, piperidin-1-yl, homopiperidin-1-yl, morpholin-4-yl, homomorpholin-4-yl, piperazin-1-yl, 4-($C_{1-3}$-alkyl)-piperazin-1-yl, homopiperazin-1-yl or 4-($C_{1-3}$-alkyl)-homopiperazin-1-yl group,
a propyloxy group which is substituted by a group $R^4$ in the 3 position, wherein $R^4$ is as hereinbefore defined, or
a butyloxy group which is substituted by a group $R^4$ in the 4 position, wherein $R^4$ is as hereinbefore defined,
$R^e$ and $R^d$ may be identical or different and denote a hydrogen atom or a methyl group
and
X denotes a nitrogen atom,
a tautomer, stereoisomer, a mixture thereof or a salt thereof.

3. The bicyclic heterocycle of formula I according to claim 1, wherein
$R^a$ denotes a hydrogen atom,
$R^b$ denotes a 3-ethynylphenyl, 3-bromophenyl, 3,4-difluorophenyl or 3-chloro-4-fluoro-phenyl group,
$R^c$ denotes a hydrogen atom,
a methoxy, ethyloxy, 2-(methoxy)ethyloxy, 3-(morpholin-4-yl)propyloxy, cyclobutyloxy, cyclopentyloxy, cyclohexyloxy, cyclopropylmethoxy, cyclopentylmethoxy, tetrahydrofuran-3-yloxy, tetrahydropyran-3-yloxy, tetrahydropyran-4-yloxy, tetrahydro-furan-2-ylmethoxy, tetrahydrofuran-3-ylmethoxy or tetrahydropyran-4-ylmethoxy group,
$R^e$ and $R^d$ denote a hydrogen atom
and
X denotes a nitrogen atom,
a tautomer, stereoisomer, a mixture thereof or a salt thereof.

4. The bicyclic heterocycle of formula I according to claim 1, wherein
$R^a$ denotes a hydrogen atom,
$R^b$ denotes a 3-chloro-4-fluoro-phenyl group,
$R^c$ denotes a tetrahydrofuran-3-yloxy group,
$R^e$ and $R^d$ denote a hydrogen atom
and
X denotes a nitrogen atom,
a tautomer, stereoisomer, a mixture thereof or a salt thereof.

5. The following compound of formula I according to claim 1:
4-[(3-chloro-4-fluoro-phenyl)amino]-6-{[4-(homomorpholin-4-yl)-1-oxo-2-buten-1-yl]amino}-7-[(S)-(tetrahydrofuran-3-yl)oxy]-quinazoline
or a salt thereof.

6. The physiologically acceptable salt of a compound according to claim 1.

7. A pharmaceutical composition comprising a compound according to claim 1 or a physiologically acceptable salt thereof and one or more inert carriers and/or diluents.

* * * * *